United States Patent
McCaffrey et al.

[11] Patent Number: 5,696,314
[45] Date of Patent: Dec. 9, 1997

[54] MULTILAYER ENZYME ELECTRODE MEMBRANES AND METHODS OF MAKING SAME

[75] Inventors: Robert McCaffrey, Franklin; Bonnie Dalzell, Sherborn; Katarina Tkacik, Concord; Susan Holbert, Holliston; Mark Boden, Millbury; James Flaherty, Attleboro; Michael Flanagan, Needham, all of Mass.; Josef Brown, Salem, N.H.; Kimiya Takeshita, Sanda, Japan; Peter Edelman, Franklin, Mass.

[73] Assignee: Chiron Diagnostics Corporation, E. Walpole, Mass.

[21] Appl. No.: 679,089

[22] Filed: Jul. 12, 1996

[51] Int. Cl.⁶ .............. G01N 27/26; G01N 33/535; G01N 33/66; H01L 29/78
[52] U.S. Cl. .............. 73/53.01; 73/61.41; 73/61.71; 73/64.47; 422/88; 435/288; 435/817; 435/14; 204/414; 204/403
[58] Field of Search .............. 73/53.01, 61.41, 73/61.71, 61.73, 61.47, 64.47; 422/88–98; 435/817, 288, 291, 14; 204/403, 414–415

[56] References Cited

U.S. PATENT DOCUMENTS

| | | | |
|---|---|---|---|
| 3,635,075 | 1/1972 | Gilbert | 73/64.3 |
| 3,661,011 | 5/1972 | Myrenne | 73/64.3 |
| 3,756,923 | 9/1973 | Dahms | 204/1 T |
| 4,238,757 | 12/1980 | Schenck | 357/25 |
| 4,267,023 | 5/1981 | Frant et al. | 204/1 T |
| 4,311,669 | 1/1982 | Spangler | 422/98 |
| 4,452,887 | 6/1984 | Katajima et al. | 435/14 |
| 4,970,145 | 11/1990 | Bennetto et al. | 435/14 |
| 5,160,418 | 11/1992 | Mullen | 204/153.12 |
| 5,212,050 | 5/1993 | Mier et al. | 430/320 |
| 5,326,449 | 7/1994 | Cunningham | 204/403 |
| 5,438,984 | 8/1995 | Schoendorfer | 128/632 |
| 5,494,562 | 2/1996 | Maley et al. | 204/403 |
| 5,547,848 | 8/1996 | Shinoki et al. | 435/7.9 |
| 5,554,339 | 9/1996 | Cozzette et al. | 422/50 |
| 5,582,698 | 12/1996 | Flaherty et al. | 204/409 |

*Primary Examiner*—Hezron E. Williams
*Assistant Examiner*—J. David Wiggins
*Attorney, Agent, or Firm*—Arthur S. Morgenstern; Stanley Sacks; Robert P. Blackburn

[57] ABSTRACT

An electrochemical sensor is designed for use in detecting a concentration of an analyte in a sample solution. The sensor to have a longer useful lifetime, improved stability and improved response time for single or multiple use applications. In one aspect, some of these goals are achieved by providing the multilayer enzyme electrode membrane having both nonporous and microporous layers. The microporous layer is formed from a polymer binder, a polymer powder, a surfactant and a mineral powder. In another aspect, certain of these goals are achieved by the use of a layer comprised of an enzyme disposed within a polymer matrix. In certain embodiments, the multilayer enzyme electrode membrane includes an outermost layer which is capable of dissolving in the sample solution such that the interface between the multilayer enzyme electrode membrane and the sample solution is continually renewed. The sensor provides an electrical current output proportional to the reagent chemical interaction of the analyte with an immobilized enzyme layer during exposure of the sensor in such solution.

55 Claims, 2 Drawing Sheets

MULTILAYER ENZYME ELECTRODE MEMBRANES AND METHODS OF MAKING SAME

1. FIELD OF THE INVENTION

The present invention relates generally to multilayer enzyme electrode membranes having a multilayer design and methods of making same, and more specifically to such membranes which provide improved response time and stability as well as longer life time in electrode sensors designed for single or multiple use purposes.

2. DISCUSSION OF THE RELATED ART

Electrode sensors designed to monitor the concentration of analytes in biological fluids, such as blood, sweat, saliva, plasma, tears and urine, are well known. In particular, electrochemical enzyme based sensors have been developed that can be used to measure the concentration of various analytes, such as glucose or lactate, in biological fluids. The ability to monitor the concentration of these analytes in biological fluids is important because, based on the concentration of lactate or glucose, a variety of potential health problems can be detected. For example, a concentration of glucose below the normal range can cause unconsciousness, lowered blood pressure and possibly even death. However, a concentration of glucose above normal can result in coma for diabetics. Furthermore, a lactate concentration above a certain level can indicate a variety of problems including hemorrhaging, dehydration, the potential onset of heart attack, sepsis and other infections.

Known enzyme electrode sensors usually include an enzyme-containing layer, which imparts specificity, deposited onto a layer of electrically conductive material which serves as the electrode. The electrically conductive material is disposed on a substrate, and a membrane structure overlays the electrode. The general goals of the membrane structure include immobilizing or entrapping the enzyme, protecting the sensor from protein fouling, screening the sensor from possible interferants and regulating analyte diffusion to linearize sensor response to analyte concentration. Typically, the membrane structure is constructed by thin or thick film techniques such as, for example, silk screening, stenciling, spinning, dipping or spraying.

Available enzyme electrode membranes are designed to allow the analyte of interest to be converted by the enzyme, forming a product. This reaction product then takes part in a reduction-oxidation reaction at the electrode, resulting in the formation of electrons. The measured current of the electrons is indicative of the analyte concentration. For example, when measuring the concentration of glucose or lactate in blood, the analyte is first oxidized by glucose oxidase or lactate oxidase, respectively, to form hydrogen peroxide as shown in reactions 1A and 1B. The hydrogen peroxide is then oxidized to create an electric current (reaction 2) that indicates the concentration of the glucose or lactate in the blood.

(1A)

(1B)

(2)

Oxidation of the analyte by the enzyme results in the formation of the reduced form of the enzyme. If an insufficient amount of oxygen is able to reach the electrode, the enzyme may remain in its reduced form, decreasing the utility of the enzyme electrode. Therefore, the materials used to form the electrode membrane should have relatively high oxygen permeabilities so that enough oxygen can reach the enzyme electrode to reconvert the enzyme from its reduced form back to its oxidized form. In addition to allowing good oxygen transport through the membrane to reconvert the enzyme, it is desirable to provide sufficient oxygen transport through the membrane so that oxygen does not serve as a limiting reagent in the overall reaction.

To provide a constant increase in signal per unit increase in analyte concentration in the analyte solution (i.e., to achieve good reproducibility), the analyte should be the rate limiting reagent. Thus, as discussed in the previous paragraph, the membrane should provide good oxygen transport. In addition, the amount of enzyme immobilized at the electrode should be enough to react with the analyte reaching the enzyme electrode without the enzyme acting as a rate limiting reagent. To achieve this goal, the membrane should be formed from materials capable of controlling the flow of the analyte through the membrane, the electrode should contain a comparatively large amount of enzyme, or both.

A sample solution may be used to calibrate enzyme electrodes by measuring the electrical current output for a fixed concentration of analyte. The sample solution used for this calibration is preferably an aqueous solution for ease of manufacturability and for enhanced storage stability (i.e., shelf life). While the sample solution used to calibrate the sensor is an aqueous solution containing low molecular weight salts, the solutions to be measured are biological fluids, such as whole blood which contains proteins and other organics. There is often an inherent difference in the response for the analyte between the enzyme electrode in the aqueous calibration sample solution and the enzyme electrode in the protein containing analyte solution. However, to ensure reliable calibration, this difference in response between the enzyme electrodes of the two solutions, commonly referred to as the blood/aqueous slope ratio, should not change over time.

Certain known enzyme electrode membranes, such as track-etched polycarbonate membranes, are capable of regulating analyte flow and decreasing protein fouling of the electrode. However, these membranes are stand alone membranes, so they cannot be easily prepared on top of a planar microsensor.

Accordingly, it is desirable to provide a multilayer enzyme electrode membrane that is formed from materials that result in a stable blood/aqueous ratio while allowing the analyte to serve as the rate limiting reagent. Furthermore, it is particularly desirable to provide such an enzyme electrode membrane that is capable of monitoring the concentration of glucose and lactate in blood.

SUMMARY OF THE INVENTION

Therefore, it is an object of the present invention to provide a multilayer enzyme electrode membrane that is capable of providing a stable blood/aqueous ratio.

It is another object of the present invention to provide a multilayer enzyme electrode membrane designed such that the analyte is the rate limiting reagent.

It is yet another object of the present invention to provide a multilayer enzyme electrode membrane that extends the uselife of the sensor.

It is still another object of the present invention to provide a multilayer enzyme electrode membrane that reduces fouling of the electrode by proteins and blocks relatively high molecular weight interferants.

It is a further object of the present invention to provide a multilayer enzyme electrode membrane having a membrane formed from more than one layer.

It is still a further object of the present invention to provide a multilayer enzyme electrode membrane having at least one microporous layer to control the flow rate of analyte through the membrane.

It is yet a further object of the present invention to provide methods of making any or all of these multilayer enzyme electrode membranes.

In one illustrative embodiment, the present invention provides a sensor for measuring a concentration of an analyte in a solution. The sensor comprises a substrate layer, an electrode layer, an immobilized enzyme layer and a microporous layer. The substrate layer is formed from an electrically insulating material and supports the electrode layer which is formed from an electrically conductive material. The immobilized enzyme layer includes an enzyme immobilized in a support member and is supported by the electrode layer. The microporous layer is formed from a polymer powder, a mineral powder and a polymer binder, and the microporous layer is supported by the immobilized enzyme and substrate layers.

In another illustrative embodiment, the present invention provides a sensor for measuring a concentration of an analyte in a solution. The sensor comprises first, second, third, fourth, fifth and sixth layers. The first layer is formed from an electrically insulating material and supports the second layer which is formed from an electrically conductive material. The third layer, which is formed from a dielectric material, is supported by the first layer. The fourth layer includes an enzyme immobilized to a support member and is supported by the second layer. The fifth layer, which is formed from a silane, is supported by the third and fourth layers. The sixth layer is formed from an enzyme disposed within a polymer matrix and is supported by the fifth layer.

In a further illustrative embodiment, the present invention provides a method of measuring a concentration of an analyte disposed within a solution which further includes at least one interferent. The method comprises the steps of: operatively engaging an electrode sensor with a solution in which the analyte is disposed by dissolvation, the electrode sensor comprising a substrate layer, an electrode layer, an immobilized enzyme layer and a microporous layer located between the immobilized enzyme layer and the solution; and passing the solution in which the analyte is disposed through the microporous layer while minimizing passage of the at least one interferent through the microporous layer to the underlying layers.

In yet a further illustrative embodiment, the present invention provides a sensor for measuring a concentration of an analyte in a solution. The sensor is formed from a substrate layer, a dielectric layer, an electrode layer and an immobilized enzyme layer. The electrode and dielectric layers are each disposed on the substrate layer, and the immobilized enzyme layer is disposed on the electrode layer. The improvement of this embodiment comprises a microporous layer formed from a polymer powder, a mineral powder and a polymer binder. The microporous layer is supported by the substrate and immobilized enzyme layers.

BRIEF DESCRIPTION OF THE DRAWINGS

The features, objects and advantages of the present invention will be better understood from the following detailed description of the invention when read in conjunction with the accompanying drawings, in which.

DETAILED DESCRIPTION

The present invention provides an electrode sensor that provides a stable blood/aqueous slope ratio while providing diffusion restriction such that the analyte is the rate limiting reagent. At least in part, the restricted diffusion is achieved by the use of at least one microporous layer which limits the transport of the analyte through the sensor. By varying the pore size of the microporous layer and/or the thickness of the microporous layer, the transport of analyte across the multilayer membrane can be controlled. Moreover, at least in part, stability of the blood/aqueous slope ratio is provided by a layer of the sensor which comprises an enzyme disposed within a polymer matrix.

Figure 1:
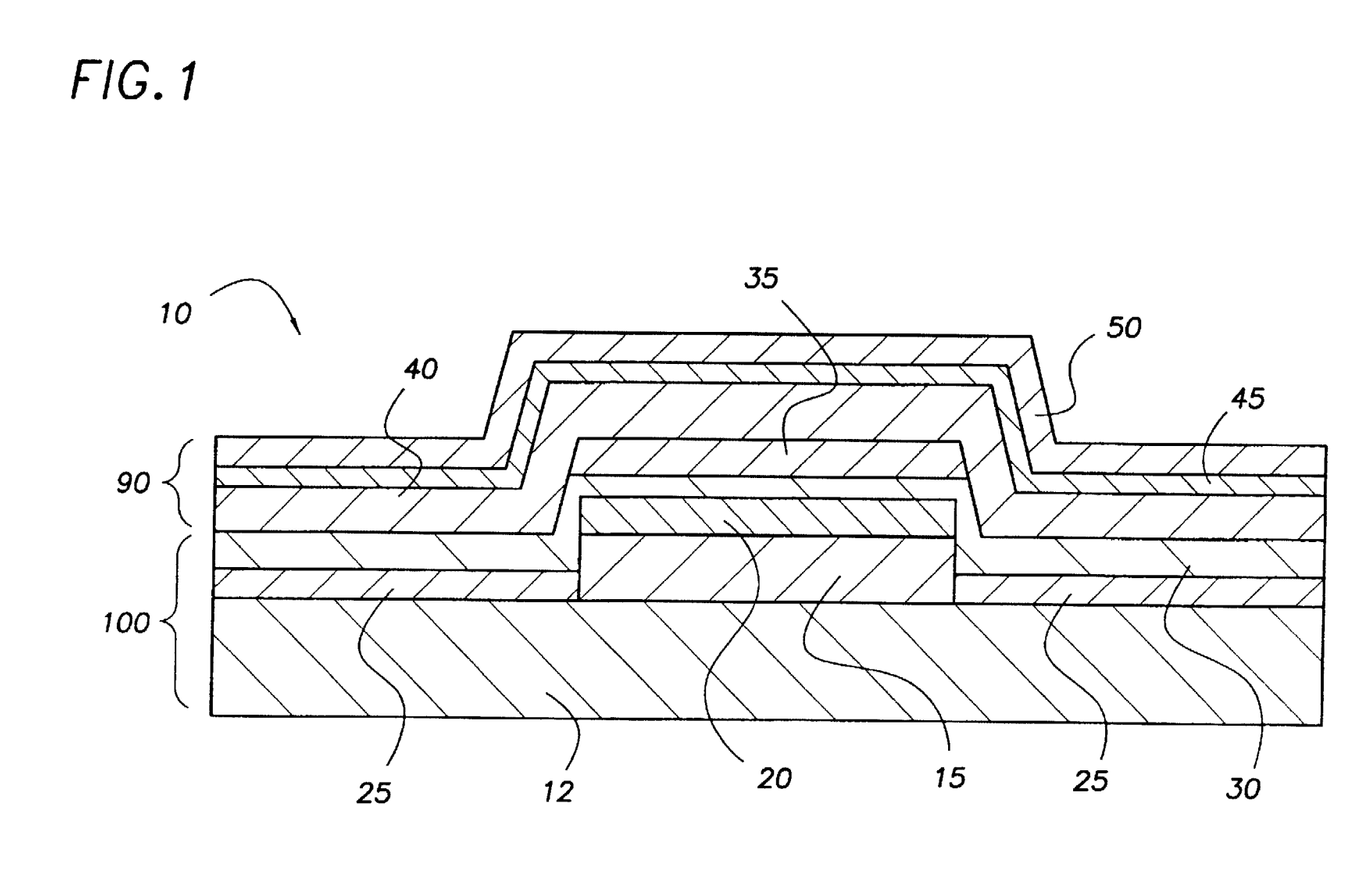
FIG. 1 is a cross sectional view of one embodiment of a multilayer enzyme electrode membrane according to the present invention.

FIG. 1 depicts a sensor 10 according to one embodiment of the present invention. Sensor 10 includes an electrode portion 90 and a membrane portion 100. Electrode portion 90 includes substrate layer 12, electrode layer 15, immobilized enzyme layer 20, a dielectric layer 25, an adhesive layer 30 and enzyme/polymer layer 35. Membrane portion 100 includes a microporous layer 40, a surfactant/polymer layer 45 and a stabilizing layer 50. The electrochemical sensor includes electronic means connected to the electrode layer for monitoring an electrical current output resulting from a reagent interaction of the analyte with the immobilized enzyme layer during exposure of the sensor to the sensor.

As shown in FIG. 1, substrate layer 12 supports layer 15 and dielectric layer 25. Adhesive layer 30 is supported by immobilized enzyme layer 20 and dielectric layer 25. Microporous layer 40 is supported by enzyme/polymer layer 35 and adhesive layer 30. Surfactant/polymer layer 45 is supported by microporous layer 40, and stabilizing layer 50 is supported by layer 45.

Substrate 12 may be formed from any substantially electrically insulating material such as, for example, ceramics, glasses, refractories, polymers or combinations thereof. Formation of such an insulating substrate as a mechanical support or base is well known to those of ordinary skill in the art. Preferably, substrate 12 is substantially formed from alumina. In a particularly preferred embodiment, substrate 12 comprises approximately 96% alumina and approximately 4% glass binder (available from Coors Ceramic Company, Grand Junction, Colo.). Substrate 12 preferably has a thickness of from about 0.02 inch to about 0.05 inch and more preferably about 0.025 inch.

Electrode layer 15 is formed from an electrically conductive material such as a metal or alloy. Preferably, layer 15 comprises a platinum group metal (platinum, palladium, iridium, rhodium) and mixtures thereof. More preferably platinum, palladium and mixtures thereof, and most preferably platinum. While particular materials appropriate for construction of layer 15 have been disclosed herein, it should be understood that this list is not limiting and that layer 15 may also comprise other electrically conductive materials. However, layer 15 should be comprised of a material which is not oxidized or reduced in a potential range in which oxidation or reduction of the analyte occurs.

Moreover, materials selective for fabrication of layer 15 are desirably free of any impurities such as battery metals (electrochemically active in water) which are typically present in the off-the-shelf materials commercially available for screen printing, wire bonding, soldering, or welding. Preferably, layer 15 has a thickness of from about 10 micrometers to about 20 micrometers and more preferably about 15 micrometers.

In a particularly preferred embodiment, layer 15 is formed from a platinum paste, such as product No. PC 10208/Pt available from Metech, Inc., located in Elverson, Pa. Other metal pastes which are appropriate for use in the formation of layer 15 will be apparent to those skilled in the art.

Located above layer 15 is immobilized enzyme layer 20 which comprises an enzyme immobilized into an electrically conducting support member which comprises a porous layer of resin-bonded carbon or graphite particles. The particles have intimately mixed therewith, or deposited or adsorbed onto the surface of the individual particles prior to bonding to form the layer, a finally divided platinum group metal. This forms a porous substrate layer into which the enzyme is immobilized and comprises a substantially heterogenous layer of resin-bonded carbon or graphite particles for the platinum group metal adsorbed on the carbon or graphite particles. An enzyme immobilized or adsorbed onto a porous layer of resin bonded platinized particles is useful in the present invention as disclosed by Mullen, in U.S. Pat. No. 5,160,418 and Bennetto et al. in U.S. Pat. No. 4,970,145, both of which are herein incorporated by reference. Immobilized enzyme layer 20 may alternatively be formed by first depositing the finally divided platinum group metal, optionally preadsorbed onto or mixed with finally divided carbon or graphite, with or without all or some of the resin binder, if used, on the surface of layer 15.

The platinum group metal in finally divided elemental form, including platinum, palladium, iridium, or rhodium, may be replaced by the corresponding oxides, such as platinum or palladium oxide. Therefore, all references herein to a platinized material are to be taken as including a platinum group metal, as described above and/or corresponding oxide, containing materials unless the context requires otherwise.

Any suitable carbon or graphite powder which readily permits the subsequent immobilization of an enzyme may be used to form immobilized enzyme layer 20. To this end, carbon powder should be used having a high density of functional groups, such as carboxylate, amino and sulfur-containing groups, on the surface, as opposed to the more vitreous and glassy carbons, which bind enzymes only poorly. Typically, carbon or graphite powder particle size ranges from between about 3.0 nm and about 50.0 nm; preferably, particle sizes ranges from between about 5.0 nm and 30.0 nm.

Platinum may be deposited on the carbon particles in any convenient fashion. For example, vapor phase deposition, electrochemical deposition or simple absorption from colloidal suspension to give platinum group metal loadings in the range of between about 0.1 to about 20.0%, by weight, based on the weight of carbon. Preferably, the platinum group metal loadings are between about 5.0 to about 15.0% by weight. These limits are, however, practical rather than critical. Below about 1.0% platinum group metal, the output signal falls to a level which, in practical terms, may be too low to be measured except by very sensitive apparatus; above about 20.0%, the loading of platinum group metal may become uneconomic, with little additional benefit in terms of increased response or sensitivity. In the preferred technique, the carbon powder is platinized by the oxidated decomposition of a platinum compound such as chloroplatinic acid or, more preferably, a complex of platinum or palladium with an oxidizable ligand, in the presence of the carbon powder, thereby to deposit colloidal size platinum or palladium directly upon the surface of the carbon particle, in the manner taught, for example, by Petrow et al., in U.S. Pat. Nos. 4,044,193 and 4,166,143, both of which are herein incorporated by reference. Preferably, the platinum group metal or oxide particles have a particle size in the range of between about 1.0 nm to about 20.0 nm, and most preferably are a colloidal size in the range of between about 1.0 nm to about 4.0 nm.

The preferred substrate materials used in immobilized enzyme layer 20 are commercially available materials, sold under the name Platinum on Carbon Black from E-TEK, Inc. located in Framingham, Mass. An enzyme, such as glucose oxidase or lactate oxidase, can be immobilized onto platinized carbon powder particles, prepared by the deposition of colloidal platinum having a particle size of between about 1.5 nm to about 2.5 nm onto the carbon powder, having a nominal size of about 30.0 nm, by the oxidated decomposition of complex platinum sulfite acid (II) using hydrogen peroxide.

In the present invention, the platinum activated carbon is treated in phosphate buffer formulation having a pH of about 7.5. The platinum activated carbon is added to the buffer to neutralize any sulfuric acid present from the formation of the platinized carbon powder particles. To the platinum activated carbon and buffer mixture a co-protein, such as bovine serum albumin, is added to adsorb onto the carbon. The bovine serum albumin is added to help stabilize the enzyme as to is known to those skilled in the art. A hydrophobic binder, such as a polyester formed from a diacid and a diol, is then added to the bovine serum albumin-platinum activated carbon mixture. One example of such a hydrophobic binder is the commercially available resin solution sold under product No. 8101RS from Metech. While particular formulations of the hydrophobic binder have been disclosed herein, it is to be understood that other hydrophobic binders are contemplated to be appropriate for use in the present invention. Such hydrophobic binders should be capable of holding the components of the active layer together after evaporation of the solvent. Preferably, these hydrophobic binders should also be able to serve as rheology modifiers that allow screen printing of the mixture with tighter resolution.

To this mixture, a surfactant may be added to provide better screen printing flow characteristics when immobilized enzyme layer 20 is screen printed upon layer 15. An additional benefit of the surfactant may be to act as a wetting agent for multilayer electrode 90 during use since immobilized enzyme layer 20 may comprise the hydrophobic binder (discussed above) which becomes difficult to wet with water after it is fully dried. The surfactant assists in facilitating the wet up of immobilized enzyme layer 20 under these conditions. According to the present invention, the surfactant material may be any liquid surfactant which is water soluble and exhibits a hydrophilic lipophilic balance (HLB) in the range of about 12 to about 16. Such materials are known to those skilled in the art, and are typically surfactant materials including alkylarylpoly ether alcohols, such as alkylphenoxypolyethoxyethanol. One such material is sold under the trademark Triton® from Union Carbide Chemicals and Plastics Company, Inc., located in Danbury, Conn. The preferred material for use in the present application is Triton® X-100 surfactant (HLB 13.5).

After these components are milled, a resin thinner may be added to adjust the viscosity of immobilized enzyme layer 20 for printing purposes. Typically, a petroleum solvent-based resin thinner is used to bring the paste viscosity within the range of between about 10,000 to about 100,000 centipoise. Resin thinners for this purpose are commercially available as product No. 8101 thinner from Metech. Typically, such thinners are mixtures of high boiling glymes and petroleum distillates. An enzyme, such as lactate oxidase or glucose oxidase, is then added to the mixture, and the final paste is screen printed upon layer 15. Other enzymes may be similarly added to the mixture to prepare an active layer specific for other analytes.

It is believed that, for embodiments in which immobilized enzyme layer 20 includes lactate oxidase as an enzyme, layer 20 may be replaced with an electro-polymerized layer of diaminobenzene disposed on layer 15.

Dielectric layer 25, which is formed from two portions, is disposed over substrate 12. When observed from a top view of sensor 10, each of the two portions of dielectric layer 25 appear as individual, elongated sheets. Preferably, these sheets have an approximately rectangular area when observed from a top view of sensor 10. The material selected for fabrication of dielectric layer 25 is desirably electrically insulating and nonporous, free of impurities which may be subjected to oxidation or reduction in the potential range of any analyte to be measured. This material is further selected so as to be free of mobile ions that would potentially carry charge and interfere with the activity of any electrolyte employed in multilayer membrane 100. Further, dielectric layer 25 should firmly adhere to substrate 12 so as to allow sensor 10 to be electrically addressable with electrical contacts such as electrical leads or the like, while effectively electrically insulating portions covered by the dielectric. Materials appropriate for use in dielectric layer 25 include, but are not limited to, ceramics, glass, refractory materials, polymeric materials or combinations thereof. A preferred, ceramic material for use in dielectric layer 25 is available as product number 9615 from E.I. duPont de Nemours & Co., Electronics Department, located in Wilmington, Del. Preferably, dielectric layer 25 has a thickness of from about 10 micrometers to about 50 micrometers and more preferably about 20 micrometers. These thicknesses are measured after firing or curing. As is known to those skilled in the art, dielectric layer 25 may be deposited on substrate 10 using a variety of techniques known to those skilled in the art such as, for example stenciling or silk screening.

Adhesive layer 30 is designed to promote adhesion between immobilized enzyme layer 20 and enzyme/polymer layer 35 as well as between dielectric layer 25 and microporous layer 40. In addition, or alternatively, adhesive layer 30 is designed to isolate layer 35 from layer 20 in order to extend the life of the enzyme disposed within layer 35 (described below). Materials that are capable of achieving these goals, and, therefore, appropriate for use as adhesive layer 30 include, but are not limited to, silanes, including aminosilanes, styryl silanes, aminoalkylalkoxysilanes, chlorosilanes, alkylsilanes and alkylalkoxysilanes. In a preferred embodiment, layer 30 is formed from aminopropyltriethoxysilane (APTES).

Layer 30 should be capable of transporting peroxide and/or lactic acid to layer 20 from the analyte solution. However, if layer 30 is too thick, the transport of peroxide and/or lactic acid to layer 20 may be limited. Therefore, adhesive layer 30 preferably has a thickness of from about 0.1 micrometers to about 1 micrometer.

Layer 30 may be applied using a variety of known techniques including coating, spraying, and dipping techniques. Because layer 30 is applied onto immobilized enzyme layer 20, it is preferable that layer 30 be applied using a process that is not harmful to the immobilized enzyme disposed within layer 20. Accordingly, in a preferred embodiment, adhesive layer 30 is formed by pouring an aqueous solution of one of the aforementioned materials on top of layers 20 and 25 (FIG. 1), letting the solution sit for a period of time, draining the solution, and removing the excess solution by spinning with a spin coating apparatus. The surface is then dried at room temperature for approximately 24 hours to remove the remaining solvent and cure the silane material. In a particularly preferred embodiment, this technique is used with a 5% by weight aqueous solution of APTES with the step of drying being performed at room temperature for a time period of about 24 hours at relative humidity of less than about 60%. It is to be noted that it has been found to be advantageous to minimize the amount of time between preparation of the solution and application of the solution. Preferably, this time period is at most about 30 minutes.

Enzyme/polymer layer 35 is designed to increase the time period over which the blood/aqueous slope sensor 10 is constant. To assist in achieving this goal, layer 35 should only be disposed in an area above the area defined by immobilized enzyme layer 20 (i.e., layer 35 should only be disposed above the analyte sensing portion of electrode 10 formed by layer 20). In particular, since sensor 10 may be part of an overall system which includes several electrodes, at least one of which may be inactive, layer 35 should be disposed such that it does not cover an inactive electrode included in a system in which layer 35 may be part (i.e., layer 35 should not cover such an inactive electrode). "Inactive electrode" as used herein refers to a correcting electrode which does not include a catalytically active quantity of a catalytically active enzyme. Typically, such electrodes include at least substrate, electrode, and immobilized enzyme layers, wherein the immobilized enzyme layer includes, for example, bovine serum albumin. Preferably, the area of layer 35, in a direction perpendicular to the cross-section shown in FIG. 1 (i.e., along a top view of sensor 10) is from about 40% to about 100% the area of layer 20, more preferably from about 50% to about 95%, and most preferably from about 60% to about 90%. Preferably, layer 35 has a thickness of from about 1 micrometer to about 30 micrometers, more preferably from about 5 micrometers to about 20 micrometers and most preferably from about 10 micrometers to about 15 micrometers.

Layer 35 should include the same enzyme that is disposed within immobilized enzyme layer 20. For example, if layer 20 includes lactate oxidase, layer 35 should also include lactate oxidase. Alternatively, if layer 20 has glucose oxidase disposed therein, layer 35 should also comprise glucose oxidase.

In addition to the enzyme, layer 35 comprises a polymer that should have a comparatively low solubility in water under the use conditions of sensor 10 (i.e., about 37° C.). Preferably, the polymer can be applied from liquid, either as a solution in water or neat. Once applied, layer 35 can be dried or cured to achieve low solubility of the polymer. Materials appropriate for use in layer 35 should also provide an environment which assists in maintaining the normal conformation of the enzyme. Thus, if the enzyme is lactate oxidase, the polymer should be capable of providing a hydrogen-bonding environment. An exemplary and nonlimiting list of polymers appropriate for use in enzyme/polymer layer 35 includes polyvinyl pyrrolidone, gelatine, polyhydroxyethylmethacrylate (PHEMA) and polyhydric alcohols, such as polyvinyl alcohol (PVOH). For some of these materials which are relatively water soluble, such as PVOH and polyvinyl pyrrolidone, it may be desirable to render them less soluble in water by crosslinking subsequent to deposition. Appropriate methods of crosslinking such materials are known to those skilled in the art and are intended to be within the scope of the present invention. With this arrangement, the enzyme of layer 35 is disposed within a polymer matrix formed by the polymer of layer 35.

In embodiments in which the enzyme in layer 35 is lactate oxidase, the polymer of layer 35 should be a polyhydric alcohol such as PVOH. Preferably, the polymer is 99.9% hydrolized PVOH (i.e., having less than about 0.1% acetate groups). It is to be noted that increasing the amount of hydrolysis makes the PVOH more difficult to dissolve in water at room temperature, but using a more soluble form of PVOH can cause multilayer membrane 100 to swell, ultimately causing the enzyme to wash out of muitilayer membrane 100. Preferably, the PVOH has a molecular weight from about 70,000 to about 300,000. PVOH having a higher molecular weight is more difficult to manipulate when preparing layer 35 as described below, and PVOH having a lower molecular weight can make the material too soluble.

Enzyme/polymer layer 35 may be prepared by the method disclosed in commonly assigned U.S. patent application Ser. No. 08/680,050, filed on even date herewith, and entitled Sensors for Measuring Analyte Concentrations and Methods of Making Same, which is hereby incorporated by reference. This method includes the following steps. A slurry of the polymer and water is formed at room temperature then heated to dissolve the polymer. The solution is cooled to room temperature and the enzyme is added. The amount of polymer dissolved in the water varies depending upon the enzyme, polymer, the molecular weight of the polymer and analyte to be detected. For example, when lactate oxidase is used as the enzyme and 99.9% hydrolized PVOH having a molecular weight of from about 70,000 to about 300,000 is used as the polymer solution, the weight percent of PVOH dissolved in the water is preferably from about 2% to about 15%, more preferably from about 5% to about 10%, and most preferably about 7%. As the molecular weight of the PVOH is decreased, the water solubility of PVOH increases. Therefore, for higher molecular weight PVOH, these ranges decrease, and, for lower molecular weight PVOH, these ranges can increase. The amount of enzyme dissolved in the PVOH/water solution varies depending upon the enzyme, the PVOH and the analyte to be detected. When the enzyme is lactate oxidase and the polymer is 99.9% hydrolized PVOH having a molecular weight of from about 70,000 to about 300,000 is used, the weight percent of lactate oxidase dissolved in the PVOH/water solution is preferably from about 2% to about 10%, more preferably from about 4% to about 8% and most preferably about 6%. These weights refer to lactate oxidase of unit activity from about 20 to about 40 units per milligram of powder. Alternatively, the lactate oxidase can be added based on activity. For example, to provide an enzyme having an activity of about 35 units per milligram, about 1000 units to about 8000 units of enzyme should be added to about 2.0 grams of 7% PVOH in water, more preferably from about 2000 units to about 7000 units of enzyme and most preferably from about 4000 units to about 5000 unites of enzyme.

Figure 2:
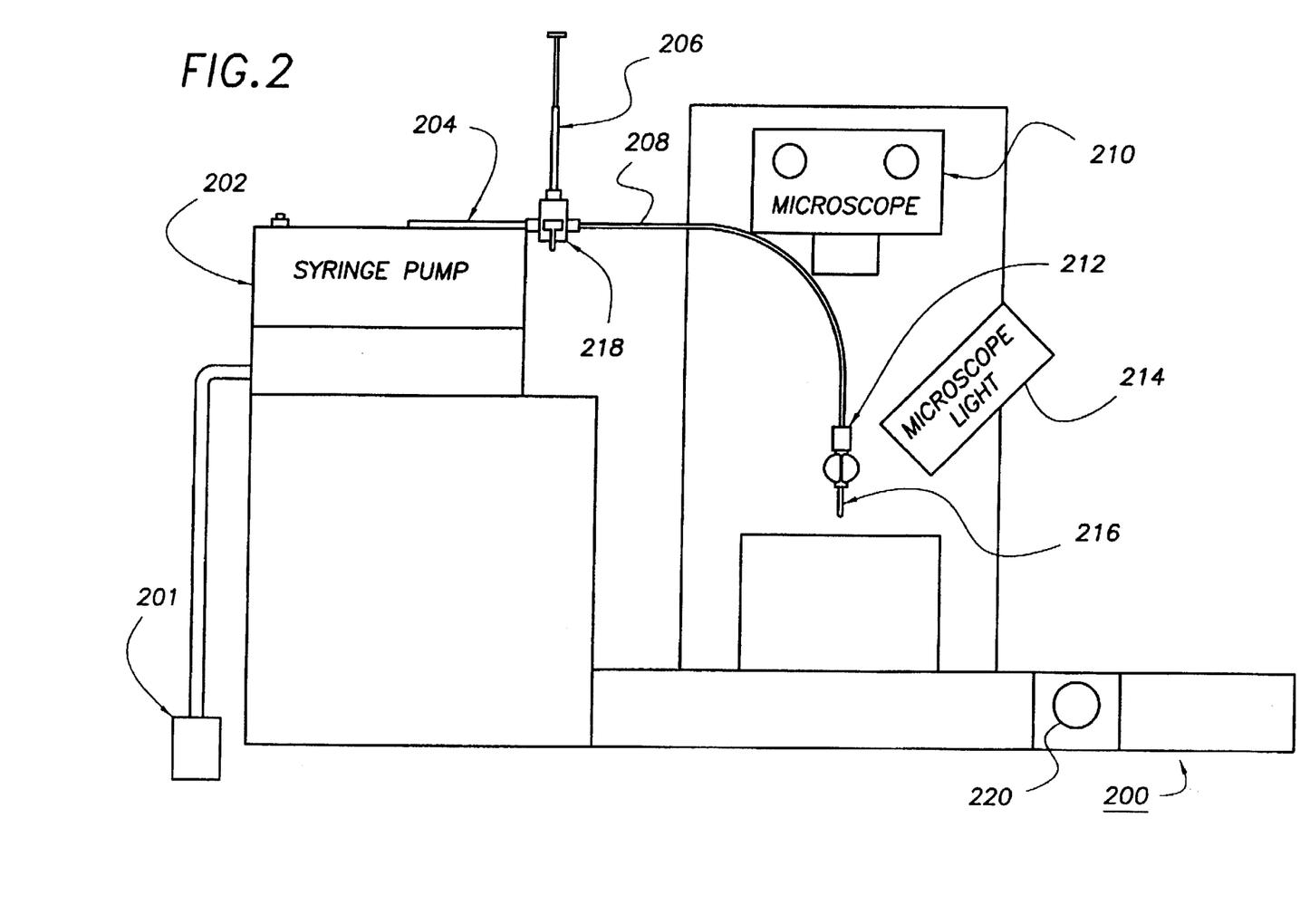
FIG. 2 is a schematic representation of one embodiment of a workstation that may be used for applying an enzyme layer according to the present invention.

Layer 35 may be applied to adhesive layer 30 using any technique known to those skilled in the art which is capable of limiting the location of layer 35 as discussed above. In a preferred embodiment, the above-described solution is applied to adhesive layer 30 using a spotting work station comprising a syringe pump with fluid connections to a dispensing needle. Such a workstation 200 is depicted in FIG. 2 and includes foot switch 201, syringe pump 202, dispensing syringe 204, filler syringe 206, tubing 208, microscope 210, male fitting 212, microscope light 214, dispensing needle 216, three-way valve 218 and vertical positioner 220. The position of layer 20 relative to the dispensing needle 216 is verified using microscope 210. When layer 30 is located beneath needle 216, foot switch 201 is depressed by the user so that syringe pump 202 dispenses a small amount of the solution used through dispensing needle 216. Typically, workstation 200 is provided such that a 20 nanoliter (nL) aliquot of solution is dispensed by needle 216, but other amounts of solution may be dispensed so long as layer 35 has the dimensions discussed herein. Subsequent to being deposited on adhesive layer 30, layer 35 should be air dried at a temperature of about 25° C. for a period time of about 1 to about 4 hours.

It is believed that the nonlinear blood/aqueous slope behavior of prior art sensors may result from diffusion of enzyme from these sensors to the solution containing the analyte. According to the present invention, layer 35 increases the amount of enzyme present in sensor 10 which may assist in delaying the onset of such nonlinear behavior by sensor 10. In addition, the polymer of layer 35 may act to immobilize the enzyme, thereby reducing the rate of diffusion of the enzyme from electrode 10 to the analyte solution. Furthermore, layer 35 may reduce the rate of diffusion of the enzyme from electrode 10 to the analyte solution by increasing the distance between immobilized enzyme layer 20 and the analyte solution.

In some embodiments, when layer 40 comprises the preferred composition as disclosed herein, sensor 10 need not include layer 45 or layer 50 (discussed below) to reduce or eliminate protein fouling of sensor 10. This can be particularly desirable when sensor 10 is used in single use applications.

Microporous layer 40 is designed to impart improved performance and increased lifetime to sensor 10. Layer 40 achieves this goal by limiting the rate at which the analyte reaches immobilized enzyme layer 20 while providing good oxygen transport so that oxygen does not function as the rate limiting reagent in the reaction which occurs at layers 20 and 35. Moreover, layer 40 is preferably capable of assisting in the prevention of fouling of immobilized enzyme layer 20, screening interferants in the analyte solution from reaching layer 20 and trapping the enzyme contained in layers 20 and 35 to reduce the rate at which the enzyme is removed from sensor 10. Preferably, layer 40 can exclude molecules having a molecular weight of at least about 10,000 from reaching layer 20. Microporous layer 40 preferably has a thickness of from about 10 micrometers to about 40 micrometers, more preferably from about 15 micrometers to about 30 micrometers and most preferably from about 20 micrometers to about 25 micrometers.

Microporous layer 40 includes a polymer powder, a mineral powder, a polymer binder and at least one surfactant. Polymer powders appropriate for use in the present invention should have relatively high oxygen transport. In addition, these polymer powders should be comparatively immiscible with most other polymer materials. Polyfluorocarbons, including the Teflon® family of polytetrafluoroethylene powders available from duPont, are appropriate for use as the polymer powder of layer 40. One example of such a fluorinated hydrocarbon polymer powder is MP1100 Teflon® (duPont). Preferably, the polymer powder has an average particle size range from about 0.02 micrometers to about 10 micrometers, more preferable from about 0.05 micrometers to about 5 micrometers, and most preferably from about 0.1 micrometers to about 1 micrometer. In a particularly preferred embodiment, the polymer powder comprises MP1100 Teflon® powder from duPont having an average particle size of about 0.2 micrometers.

The mineral powder may be any inert, solid material capable of increasing the hydrophilicity of layer 40. Since surfactants, discussed below, may dissolve out of multilayer membrane 100 of the present invention over time, the mineral powder of layer 40 allows multilayer membrane 100 to remain wetted over relatively long periods of exposure to the analyte solution. Such powders include alumina powder, silica powder, metal oxide powders, powders of polymeric materials and combinations thereof. Preferably, the mineral powder comprises alumina powder. The mineral powder preferably has an average particle size range of from about 0.1 micrometers to about 5 micrometers, more preferably from about 0.2 micrometers to about 3 micrometers, and most preferably from about 0.3 micrometers to about 1 micrometer. In a particularly preferred embodiment, the mineral powder comprises α-alumina powder, purchased in the form of an emulsion and having an average particle size of about 0.3 micrometers (product number 40-6352-006, available from Buehler Laboratory, located in Lake Bluff, Ill.). It is to be noted that this mineral powder has been found to be advantageous because it assists in maintaining the mechanical integrity of sensor 10 (i.e., this mineral powder helps the layers of sensor 10 stick together).

The polymer binder of composite layer 40 should be compatible with the polymer powder of layer 40. For example, if the polymer comprises a Teflon® powder, an appropriate polymer binder is a perfluorohydrocarbon binder. Such perfluorohydrocarbon polymer binders include Teflon® AF 1600 polymer binder available from duPont.

It is believed that the surfactant in layer 40 allows multilayer membrane 100 to hydrate upon first exposure to the analyte solution. Thus the surfactant should be compatible with water. Moreover, the surfactant of layer 40 should improve the compatibility between the polymer powder and the mineral powder. Typically, the surfactant is a non-ionic surfactant. Such non-ionic surfactants are preferably fluorinated alkyl alkoxylate non-ionic surfactants, such as FC-171 Fluorad® surfactant from the 3-M Company, located in St. Paul, Minn. Other surfactants appropriate for use in layer 40 are known to those skilled in the art and are intended to be within the scope of the present invention.

In preparing layer 40, one or more solvents may be used to form a slurry or emulsion which includes the polymer powder, the polymer binder, the surfactant and the mineral powder. The solvents used in preparing layer 40 may be any solvents so long as they are capable of dissolving the polymer binder of layer 40. In addition, the solvent should be innocuous to the enzyme. Preferably, the solvents of layer 40 have comparatively high boiling points so that screen printing or stenciling may be used when applying layer 40. Thus, if sensor 10 includes lactate oxidase and layer 40 includes a fluorinated hydrocarbon polymer powder as well as a fluorinated hydrocarbon polymer binder, appropriate solvents for layer 40 include fluorinated hydrocarbons. Preferably, the solvent is a perfluorinated hydrocarbon having about 12 carbon atoms. In a preferred embodiment, the solvents of layer 40 comprise FC-43 Fluorinert® solvent and FC-70 Fluorinert® solvent, both available from 3-M.

According to one embodiment, composite layer 40 is formed by dissolving the polymer binder in a solution formed from the solvent(s). The surfactant is then added followed by the polymer powder and the mineral powder. To reduce the agglomerate size of the resulting mixture, the mixture may be roll milled, ball milled, or otherwise manipulated to decrease the agglomerate size of the mixture. This mixture is then applied to portions of adhesive layer 30 and enzyme/polymer layer 35 as indicated in FIG. 1 using any of a variety of techniques known to those skilled in the art such as spin coating, dipping, spraying, screen printing or stenciling. In a preferred embodiment, the mixture is stenciled onto layers 30 and 35 using a 0.002 inch thick stainless steel stencil pattern. Although not shown in the figures, sensor 10 is typically part of a wafer which may comprise a plurality of such sensors (typically about 40). For such embodiments, stenciling layer 40 confines this layer over the electrode areas of sensor 10. This process is analogous to screen printing except that a stencil is used instead of a screen. Subsequent to being applied, layer 40 should be air dried under conditions of about 20° C. to about 25° C. and about 35% relative humidity to about 60% relative humidity.

Preferably, microporous layer 40 has an alumina percentage of from about 5% to about 70%, more preferably from about 10% to about 60% and most preferably from about 20% to about 50%. By "alumina percentage" it is herein meant to refer to the weight of alumina within layer 40 divided by the sum of the weights of the alumina and the polymer powder in layer 40. Microporous layer 40 preferably has a filler to binder ratio of from about 20:1 to about 1:4, more preferably from about 10:1 to about 1:2 and most preferably from about 7:1 to about 1:1. "Filler to binder ratio" herein denotes the ratio of the sum of the weights of the alumina and polymer powder in layer 40 to the weight of the polymer binder in layer 40.

It is to be noted that, since fluorinated hydrocarbons are relatively hydrophobic, the successful implementation of these materials in layer 40 was surprising because it would not be expected that these hydrophobic materials could be incorporated into multilayer membrane 100 which, in at least certain embodiments, is designed to transport hydrophilic solutions.

Surfactant/polymer layer 45 should be capable of providing improved adhesion between layer 40 and layer 50. Accordingly, layer 45 may be formed from a polymeric material and a surfactant selected such that layer 45 is compatible with both layers 40 and 50. The polymeric material of layer 45 is often the same polymeric material as used in layer 50 (discussed below). Thus, an illustrative and nonlimiting list of polymeric materials appropriate for use in the preparation of layer 45 includes polyvinyl pyrrolidone, gelatin, PVOH and HEMA. When layer 50 includes PVOH, the polymeric material of layer 45 is preferably PVOH. For such embodiments, the PVOH used in the preparation of layer 45 preferably has from about 1 weight percent to about 10 weight percent solids, more preferably from about 2.5 weight percent to about 7 weight percent solids, and most preferably about 5 weight percent solids (based on the total weight of the solution of PVOH and surfactant).

The surfactant of layer 45 may comprise any material capable of improving the adhesion between layers 40 and 50 while not substantially decreasing the advantageous features of sensor 10 as described herein. Preferably, the surfactant is a nonionic surfactant. Hence, the surfactant of layer 45 may comprise perfluorinated alkylalkoxylate surfactants. Such surfactants include, for example, FC-171 Fluorad®, FC-430 Fluorad® and FC-176 Fluorad® (all available from 3M). Other such surfactants are known to those skilled in the art and are intended to be within the scope of the present invention. In a preferred embodiment, the surfactant of layer 45 is a fluorinated alkyl alkoxylate nonionic surfactant such as FC-171 Fluorad® from 3-M. Preferably, layer 45 comprises from about 0.01 weight percent to about 1 weight percent nonionic surfactant, more preferably from about 0.05 weight percent to about 0.5 weight percent nonionic surfactant, and most preferably about 0.1 weight percent nonionic surfactant (based on the total weight of the solution of polymeric material and surfactant).

To optimize the performance of sensor 10, layer 45 should have a thickness of from about 0.5 micrometers to about 5 micrometers, more preferably from about 1 micrometer to about 3 micrometers and most preferably about 1 micrometer. In a particularly preferred embodiment, layer 45 has a thickness of about 1 micrometer and comprises about 0.1 weight percent FC-171 Fluorad® and about 5 weight percent PVOH.

Layer 45 may be applied to layer 40 using any of a variety of standard techniques known to those skilled in the art. Such techniques include, for example, spin coating, dipping and spraying. Preferably, layer 45 is applied to layer 40 by spin coating. Layer 45 should be dried prior to the application of layer 50 (discussed below). In one embodiment, layer 45 is air dried for about 15 minutes at room temperature.

Stabilizing layer 50 is designed to effect minimal protein adsorption. Layer 50 can continually provide a fresh surface of multilayer membrane 100 at the interface of multilayer membrane 100 with the analyte solution so that it is difficult for proteins within the analyte solution to adsorb to the outer surface of multilayer membrane 100 (i.e., to reduce fouling of sensor 10). Accordingly, layer 50 may be formed from any hydrophilic, water permeable polymeric material capable of minimizing protein adsorption. This can be achieved by forming a renewable surface at the interface between multilayer membrane 100 and the analyte solution interface, depending upon the composition of the analyte solution. For example, when the analyte solution comprises blood, layer 50 typically is formed from a polymeric material that is at least partially soluble in water so that the polymeric material slowly washes out into the analyte solution over time, constantly providing a new surface at the interface between multilayer membrane 100 and the analyte solution.

Polymeric materials appropriate for use in the preparation of layer 50 include, but are not limited to, polyvinyl pyrrolidone, gelatine PHEMA and PVOH. Preferably, layer 50 is formed using PVOH having from about 5 weight percent to about 25 weight percent solids, more preferably from about 8 weight percent to about 12 weight percent solids and most preferably about 10 weight percent solids.

The thickness of layer 50 should be chosen so as to optimize the advantageous features of the present invention as described herein. Preferably, layer 50 has a thickness of from about 5 micrometers to about 20 micrometers, more preferably from about 8 micrometers to about 12 micrometers and most preferably about 10 micrometers.

Layer 50 may be formed according to a variety of processes known to those skilled in the art including, for example, spin coating, spraying and dipping techniques. Preferably, layer 50 is formed by spin casting the polymeric material of layer 50 onto layer 45, followed by drying. In certain embodiments, layer 50 may be air dried for about 15 minutes at room temperature.

Multilayer membranes according to the present invention can further include the typical elements that are used for such multilayer membranes including, for example, electrical leads, electrically non-conductive (insulating) supports or probes and other such elements which are known to those skilled in the art.

The following example describes one embodiment of the present invention and is not to be construed as limiting to the present invention.

EXAMPLE

The electrically insulating substrate layer was formed from about 96% alumina and about 4% glass binder, available from Coors Ceramic Company, Grand Junction, Co. The electrode layer was applied to the substrate layer as a 10 micrometer emulsion of high purity platinum paste, available as product number PC 10208 from Metech, via screen printing with a 325 mesh stainless steel screen. A BTU zone furnace with a three zone dryer, from Fast Fire of Billerica, Mass., was used in firing the platinum emulsion. Firing was carried out per the manufacturer's recommendations, and the temperature was ramped to 750° C. for a thirteen minute peak.

The dielectric layer was screen printed as a 15 micrometer emulsion over portions of the substrate layer not covered by the electrode layer using a 325 mesh stainless steel screen. The material used for the dielectric layer was product number 9615 from duPont Electronics, Wilmington, Del. Subsequent to application on the substrate layer, the dielectric layer was fired at 750° C. for a ten minute peak.

An immobilized enzyme layer was deposited on the electrode layer using a screen printing method. The immobilized enzyme layer comprised a catalytically active quantity of lactate oxidase (catalog number 1381, Genzyme, Cambridge, Mass.) immobilized with platinized carbon powder particles, available from E-TEK, Inc., Framingham, Mass.

An aqueous solution of APTES was made by pipetting about 1 gram of APTES (product number A0750, United Chemical Technolgies, Bristol, Pa.) into a container and adding about 19 grams of deionized water. This mixture was capped, shaken and allowed to stand for about five minutes. The dielectric and immobilized enzyme layers were then flooded with APTES solution and allowed to react for about ninety seconds. Excess solution was drained after this time period, and the sensor was spun on an Integrated Technologies spin coater at about 4000 revolutions per minute for about ninety seconds. The solution was then dried at room temperature and less than about 60% relative humidity for about 24 hours to form the adhesive layer.

The enzyme polymer layer Was prepared as follows. First, a slurry of about 0.7 grams of PVOH in about 9.3 grams of deionized water by mixing the liquids at room temperature. The PVOH was about 99.9% hydrolyzed PVOH having an average molecular weight of from about 89,000 to about 98,000 (product number 34,158-4, Aldrich, Milwaulkee, Wis.). The slurry was boiled to dissolve the PVOH and then cooled to room temperature. About 2 grams of this PVOH solution was added to about 0.08 grams of lactate oxidase (catalog number 1381, Genzyme, Cambridge, Mass.) at room temperature, and the lactate oxidase was dissolved by gently rolling by the container by hand.

This solution was applied to the adhesive layer using a spotting workstation which comprised a modified wire bonder (part number 827, Mech-El Industries, Woburn, Mass.) from which the ultrasonic box was disconnected, and the wire clamp, capillary, spool and chuck heater were removed. The wire capillary was replaced with a collet that mounts the dispensing needle (described below) to provide a manual pick and place mechanism, and a set of shelves was mounted on the right side of the workstation to support the syringe pump. The workstation included a microscope, a syringe pump (part number 74900, Cole Palmer Instrument Co., Niles, Ill.), a fifty microliter dispensing syringe (part number 1705, Hamilton), a one milliliter filler syringe (Moject) and a dispensing needle (part number Blunt-26G-7/16, Popper and Sons, New Hyde Park, N.Y.). Female Luer lock fittings (part number 20055, Alltech, Deerfield, Ill.) were used to connect the dispensing syringe and the filler syringe to a three way valve (part number 86727, Alltech). A PEEK ferrule (part number 20114, Alltech) joined PEEK compression fitting (part number 20124, Alltech) to the three way valve and to about twelve inches of 0.31 inner diameter PEEK tubing (part number 35710, Alltech). The PEEK tubing was connected to a PEEK ferrule (part number 20114, Alltech) and PEEK compression firing which was connected to a PEEK union fitting (part number 20088, Alltech). A male Luer lock fitting (part number 90044, Alltech) connected the PEEK union fitting to the dispensing needle. The syringe pump was in communication with a footswitch such that depression of the footswitch resulted in dispensation of solution from the dispensing needle. The microscope was positioned adjacent the dispensing needle such that, when an aliquot of a solution was dispensed from the dispensing needle onto a surface (discussed below), the resulting surface could be observed through the microscope.

A portion of the lactate oxidase/PVOH solution was disposed within the syringe pump, and the dispensing needle was positioned adjacent the adhesive layer in an area above the immobilized enzyme layer. The foot pedal was tapped to dispense an aliquot of about 0.02 microliters of the solution onto the adhesive layer such that the solution covered an area of from about 60% to about 90% of the area of the immobilized enzyme layer.

The microporous layer was made by first preparing a solution of Teflon® AF1600 polymer binder (duPont) in FC-43 Fluorinert® solvent (3M) by pipetting about 15 grams of the solvent into a container in which about 0.963 grams of the polymer binder was disposed. This mixture was heated to from about 60° C. to about 70° C. for about eight hours until the binder was dissolved. The α-alumina powder (product number 40-6352-006, available from Buehler Laboratory, located in Lake Bluff, Ill.) was next prepared by heating in a drying oven to about 80° C. for from about sixteen to about twenty hours to dry this slurry. About 0.119 grams of FC-171 surfactant (3M), about 8.3 grams of the binder solution, about 6.2 grams of FC-43 solvent (3M), about 4.28 grams of Teflon® MP1100 powder (duPont) and about 1.07 grams of dried α-alumina were sequentially added to a container. 41 tungsten carbide beads were added to this mixture, and the container was capped and turned upside down to wet the beads. The mixture was then roll milled for from about sixteen to about twenty hours to form an ink. The ink was then manually stenciled using an ADI Hand Stenciler to form the microporous layer.

The stabilizing layer was prepared by making a 10% by weight aqueous solution of solution according to the method described above but using about 45 grams of deionized water and about 5 grams of PVOH. The microporous layer was flooded with this solution using an Eppendorf repeater pipetter with a 250 microliter syringe. The sensor was then placed on a Integrated Technologies spin coater and spun at about 4000 revolutions per minute for about four minutes. The sensor was then dried under atmospheric conditions.

Having thus described certain embodiments of the present invention, various alterations, modifications and improvements will be obvious to those skilled in the art. Such variations, modifications and improvements are intended to be within the spirit and scope of the invention. The materials employed, as well as their shapes and dimensions, may be any required. Accordingly, the foregoing description is by way of example only and is not intended as limiting. The invention is limited only as defined in the following claims and the equivalents thereto.

What is claimed is:

1. A sensor for measuring a concentration of an analyte in a solution, the sensor comprising:
 a substrate layer formed from an electrically insulating material;
 an electrode layer formed from an electrically conductive material, the electrode layer being disposed over and supported by the substrate layer;
 an immobilized enzyme layer including an enzyme immobilized in a support member, the immobilized enzyme layer being disposed over and supported by the electrode layer;
 a microporous layer formed from a polymer powder, a mineral powder and a polymer binder, the microporous layer being disposed over and supported by the immobilized enzyme and substrate layers.

2. A sensor in accordance with claim 1, further comprising an adhesive layer disposed between the immobilized enzyme layer and the microporous layer.

3. A sensor in accordance with claim 2, wherein the adhesive layer is formed from a silane.

4. A sensor in accordance with claim 2, wherein the adhesive layer is formed from aminopropyltriethoxysilane.

5. A sensor in accordance with claim 1, wherein the enzyme of the immobilized enzyme layer is lactate oxidase.

6. A sensor in accordance with claim 5, further comprising an enzyme-polymer layer including lactate oxidase disposed in a polymer matrix of said enzyme polymer layer, the enzyme polymer layer being disposed above the immobilized enzyme layer.

7. A sensor in accordance with claim 1, further comprising an enzyme-polymer layer including an enzyme disposed in a polymer matrix of said enzyme-polymer layer, the enzyme polymer layer being disposed above the immobilized enzyme layer.

8. A sensor in accordance with claim 7, wherein the enzyme of the enzyme-polymer layer is lactate oxidase.

9. A sensor in accordance with claim 7, wherein the enzyme-polymer layer further comprises a polymer.

10. A sensor in accordance with claim 9, wherein the polymer of the enzyme-polymer layer is capable of assisting in maintaining a natural conformation of the enzyme of the enzyme-polymer layer.

11. A sensor in accordance with claim 9, wherein the polymer of the enzyme-polymer layer is a polyhydric alcohol.

12. A sensor in accordance with claim 1, further comprising a surfactant-polymer layer comprising a surfactant and a polymer.

13. A sensor in accordance with claim 12, wherein the surfactant is a non-ionic surfactant.

14. A sensor in accordance with claim 13, wherein the non-ionic surfactant is a perfluorinated alkylalkoxylate.

15. A sensor in accordance with claim 12, wherein the polymer of the surfactant-polymer layer is selected from the group consisting of polyvinyl pyrrolidones, gelatins, polyvinyl alcohols, polyhydroxyethylmethacrylate and mixtures thereof.

16. A sensor in accordance with claim 15, wherein the polymer of the surfactant-polymer layer is a polyvinyl alcohol.

17. A sensor in accordance with claim 1, further comprising a stabilizing layer formed from a polymer.

18. A sensor in accordance with claim 17, wherein the polymer of the stabilizing layer is selected from the group consisting of polyvinyl pyrrolidones, gelatins, polyvinyl alcohols, polyhydroxyethylmethacrylate and mixtures thereof.

19. A sensor in accordance with claim 18, wherein the polymer of the stabilizing layer is a polyvinyl alcohol.

20. A sensor in accordance with claim 1, wherein the microporous layer further includes a surfactant.

21. A sensor for measuring a concentration of an analyte in a solution, the sensor comprising:

a first layer formed from an electrically insulating material;

a second layer formed from an electrically conductive material, the second layer being disposed over and supported by the first layer;

a third layer formed from a dielectric material, the third layer being disposed over and supported by the first layer;

a fourth layer including an enzyme immobilized in a support member or matrix of said fourth layer, the fourth layer being disposed over and supported by the second layer;

a fifth layer formed from a silane, the fifth layer being disposed over and supported by the third and fourth layers;

a sixth layer formed from an enzyme disposed within a polymer matrix, the sixth layer being disposed over and supported by the fifth layer.

22. A sensor in accordance with claim 21, wherein the sixth layer is only disposed in a region above the fourth layer.

23. A sensor in accordance with claim 21, further comprising a seventh layer disposed over and supported by the fifth and sixth layers, the seventh layer formed from a polymer powder, a mineral powder and a polymer binder.

24. A sensor in accordance with claim 23, wherein the polymer binder is a fluorinated hydrocarbon.

25. A sensor in accordance with claim 23, wherein the polymer powder is a fluorinated hydrocarbon powder.

26. A sensor in accordance with claim 23, wherein the polymer powder is a perfluorinated hydrocarbon polymer powder.

27. A sensor in accordance with claim 26, wherein the polymer powder has an average particle size of from about 0.2 micrometers to about 10 micrometers.

28. A sensor in accordance with claim 27, wherein the mineral powder is alumina powder, first layer is formed from alumina, the second layer is formed from platinum, the third layer is formed from a ceramic, the fourth layer includes lactate oxidase, the fifth layer is formed from aminopropyltriethoxysilane and the sixth layer include lactate oxidase.

29. A sensor in accordance with claim 23, wherein the polymer powder has an average particle size of from about 0.2 micrometers to about 10 micrometers.

30. A sensor in accordance with claim 23, wherein the mineral powder is an alumina powder.

31. A sensor in accordance with claim 30, wherein the mineral powder has an average particle size of from about 0.01 micrometers to about 5 micrometers.

32. A sensor in accordance with claim 23, further comprising an eighth layer having a surfactant and a polymer, the eighth layer being supported by the seventh layer.

33. A sensor in accordance with claim 32, wherein the polymer of the eighth layer is a polyvinyl alcohol.

34. A sensor in accordance with claim 32, wherein the surfactant of the eighth layer is a non-ionic surfactant.

35. A sensor in accordance with claim 32, wherein the surfactant of the eighth layer is a nonionic perfluoronated alkyl alkoxylate compound.

36. A sensor in accordance with claim 23, further comprising a ninth layer formed from a polymer, the ninth layer being supported by the eighth layer.

37. A sensor in accordance with claim 36, wherein the ninth layer is formed from a polyvinyl alcohol.

38. A sensor in accordance with claim 37, wherein the eighth layer is formed from a polyvinyl alcohol and a non-ionic perfluoronated alkyl alkoxylate surfactant.

39. A sensor in accordance with claim 38, wherein the polymer binder of the seventh layer is a perfluoronated hydrocarbon polymer, the polymer powder of the seventh layer is a perfluoronated polymer having an average particle size of from about 0.2 micrometers to about 10 micrometers, and the mineral powder of the seventh layer is an alumina powder having an average particle size of about 3 micrometers.

40. A sensor in accordance with claim 39, wherein the enzyme is lactate oxidase and the polymer of the sixth layer is a polyvinyl alcohol.

41. A sensor in accordance with claim 40, wherein the silane is aminopropyltriethoxysilane.

42. A method of measuring a concentration of an analyte disposed within a solution, the solution further containing at least one interferant, the method comprising the steps of:

operatively engaging an electrode sensor with the solution in which the analyte is disposed, the electrode sensor comprising a substrate layer, an electrode layer, an immobilized enzyme layer and a selectively permeable microporous layer formed from a polymer powder, a polymer binder and a mineral powder, the microporous layer being located between the immobilized enzyme layer and the solution;

passing the solution in which the analyte is disposed through the microporous layer while minimizing passage of the at least one interferant through the microporous layer to the electrode layer.

43. A method in accordance with claim 42, wherein said sensor comprises an adhesive layer and said microporous layer, and wherein said method further comprises the step of passing the solution in which the analyte is disposed through said adhesive layer formed from a silane.

44. A method in accordance with claim 43, wherein the step of passing the solution through the adhesive layer includes passing the solution through an adhesive layer formed from aminopropyltriethoxysilane.

45. A method in accordance with claim 42, further comprising the step of passing the solution in which the analyte is disposed through a surfactant layer formed from a surfactant and a polymer.

46. A method in accordance with claim 42, further comprising the step of passing the solution in which the analyte is disposed through an outer layer formed from a polymer which is capable of dissolving in a solvent of the polymer.

47. In a sensor for measuring a concentration of an analyte in a solution, the sensor being formed from a substrate layer, a dielectric layer, an electrode layer and an immobilized enzyme layer, wherein the electrode layer is disposed over a first area on the substrate layer, the dielectric layer is disposed over a second area adjacent said first area on the substrate, and the immobilized enzyme layer is disposed on the electrode layer, and wherein the improvement comprises:

a microporous layer formed from a polymer powder, a mineral powder and a polymer binder, the microporous layer being supported by the substrate and immobilized enzyme layers.

48. A sensor in accordance with claim 47, further comprising an enzyme-polymer layer including an enzyme, the enzyme-polymer layer being disposed in a polymer matrix of said enzyme-polymer layer between the immobilized enzyme layer and the microporous layer.

49. A sensor in accordance with claim 48, wherein the enzyme of the enzyme-polymer layer is lactate oxidase.

50. A sensor in accordance with claim 48, wherein the enzyme-polymer layer further includes a polymer matrix.

51. A sensor in accordance with claim 50, wherein the polymer matrix of the enzyme-polymer layer is capable of assisting in maintaining a natural conformation of the enzyme of the enzyme-polymer layer.

52. A sensor in accordance with claim 50, wherein the polymer of the enzyme-polymer layer is a polyhydric alcohol.

53. A sensor in accordance with claim 50, wherein the polymer of the enzyme-polymer layer is a polyvinyl alcohol.

54. A sensor in accordance with claim 47, wherein the microporous layer further includes a surfactant.

55. A sensor in accordance with claim 47, further comprising an adhesive layer formed from a silane, the adhesive layer being disposed between the microporous layer and the immobilized enzyme layer.

* * * * *